US010857315B2

(12) United States Patent
Brown

(10) Patent No.: US 10,857,315 B2
(45) Date of Patent: Dec. 8, 2020

(54) INHALATION DEVICE AND METHOD FOR INHALING POWDERS

(71) Applicant: David Brown, Helsinki (FI)

(72) Inventor: David Brown, Helsinki (FI)

(*) Notice: Subject to any disclaimer, the term of this patent is extended or adjusted under 35 U.S.C. 154(b) by 497 days.

(21) Appl. No.: 15/119,128

(22) PCT Filed: Feb. 20, 2015

(86) PCT No.: PCT/US2015/016720
§ 371 (c)(1),
(2) Date: Aug. 16, 2016

(87) PCT Pub. No.: WO2015/127147
PCT Pub. Date: Aug. 27, 2015

(65) Prior Publication Data
US 2017/0065779 A1 Mar. 9, 2017

Related U.S. Application Data

(60) Provisional application No. 61/942,657, filed on Feb. 21, 2014.

(51) Int. Cl.
*A61M 15/00* (2006.01)
*A61M 11/02* (2006.01)
*B05B 11/06* (2006.01)

(52) U.S. Cl.
CPC ........ *A61M 15/0098* (2014.02); *A61M 11/02* (2013.01); *A61M 15/003* (2014.02);
(Continued)

(58) Field of Classification Search
CPC ......... A24F 47/002; A45D 6/06; A61K 9/007; A61K 9/0075; A61K 9/1688; A61K 9/1694; A61M 11/001; A61M 11/003; A61M 15/00; A61M 15/0006; A61M 15/002; A61M 15/0028; A61M 15/0036; A61M 15/0041; A61M 15/0043; A61M 15/0045; A61M 15/0065; A61M 15/02; A61M 15/06; A61M 15/08; A61M 2202/062; A61M 2202/064; A61M 2205/6081;
(Continued)

(56) References Cited

U.S. PATENT DOCUMENTS 32,789 A * 7/1861 Segnitz
39,678 A * 8/1863 Russell
(Continued)

FOREIGN PATENT DOCUMENTS

GB 2405350 A 3/2005
JP 2004522519 A 1/2001
(Continued)

*Primary Examiner* — Annette Dixon
(74) *Attorney, Agent, or Firm* — Jacob Eisenberg

(57) ABSTRACT

To disperse inhaling powders, a powder is positioned in a passage of a device for dispersing powders, wherein the passage has one or more exits, one or more inlets and one or more obstructions to block the movement or to contain the powder within the device before use. A breaching pressure differential between the one or more exits and the one or more inlets of the passage is applied to breach the one or more obstructions, which fully or partially aerosolizes the powder, thus releasing a fully or partially aerosolized powder from the device.

20 Claims, 7 Drawing Sheets

(52) U.S. Cl.
CPC ....... *A61M 15/0031* (2014.02); *B05B 11/062* (2013.01); *A61M 15/0003* (2014.02); *A61M 2202/064* (2013.01); *A61M 2206/10* (2013.01); *A61M 2209/06* (2013.01)

(58) Field of Classification Search
CPC ..... A61M 2209/06; B41J 29/13; C07B 59/00; C07C 233/88; C07D 217/26; C07D 493/22; C09D 11/30; C12N 15/8249; C12N 9/0006; C12N 9/1025; C12N 9/1029; C12N 9/1096; C12N 9/18; C12N 9/88; E05B 65/087; E05C 1/16; F28D 15/0275; G03B 15/05; G03B 2215/0507; G03B 2215/0578; G03B 2215/0582; G03B 2215/0592; G06F 17/30684; G06F 9/54; H04L 29/06; H04L 29/12113; H04L 61/1541; H04L 63/08; H04L 63/102; H04L 63/104; H04L 67/16; H04L 67/306; H04L 67/34; H04L 67/36; H04L 67/42; H04L 69/24; H04L 69/329; Y10T 137/5196
USPC ............ 128/200.24, 202.13, 202.21, 203.12, 128/203.15, 203.21, 203.22, 203.23, 128/203.28, 204.13; 131/270, 271, 273; 604/58
See application file for complete search history.

(56) References Cited

U.S. PATENT DOCUMENTS

| | | | |
|---|---|---|---|
| 2,503,732 A | 4/1950 | Heisterkamp | |
| 2,642,063 A | 6/1953 | Brown | |
| 2,672,144 A * | 3/1954 | Cohen | A61M 15/0028 222/4 |
| 3,831,606 A | 8/1974 | Damani | |
| 3,948,264 A | 4/1976 | Wilke et al. | |
| 4,200,099 A | 4/1980 | Guenzel et al. | |
| 4,240,418 A | 12/1980 | Rosskamp et al. | |
| 4,265,236 A * | 5/1981 | Pacella | A61M 15/08 128/202.13 |
| 4,387,474 A * | 6/1983 | Schierloh | A01K 51/00 449/10 |
| 4,524,769 A | 6/1985 | Wetterlin et al. | |
| 5,113,855 A | 5/1992 | Newhouse | |
| 5,161,524 A | 11/1992 | Evans | |
| 5,301,666 A | 4/1994 | Lerk et al. | |
| 5,327,883 A | 7/1994 | Williams et al. | |
| 5,349,947 A | 9/1994 | Newhouse et al. | |
| 5,388,572 A | 2/1995 | Mulhauser et al. | |
| 5,441,060 A * | 8/1995 | Rose | A24F 47/002 128/202.21 |
| 5,483,954 A * | 1/1996 | Mecikalski | A61M 15/0028 128/200.24 |
| 5,513,630 A | 5/1996 | Century | |
| 5,699,789 A * | 12/1997 | Hendricks | A61M 15/0065 128/203.15 |
| 5,724,959 A | 3/1998 | McAughey et al. | |
| 5,727,546 A | 3/1998 | Clarke et al. | |
| 5,797,392 A * | 8/1998 | Keldmann | A61M 15/0028 128/203.12 |
| 5,875,776 A | 3/1999 | Vaghefi | |
| 6,098,619 A * | 8/2000 | Britto | A61M 11/003 128/203.12 |
| 6,722,364 B2 * | 4/2004 | Connelly | A61M 15/0028 128/200.23 |
| 7,040,316 B2 * | 5/2006 | Connelly | A61M 15/0028 128/203.12 |
| 7,540,285 B2 * | 6/2009 | Connelly | A61M 15/0028 128/203.12 |
| 8,459,257 B2 * | 6/2013 | Connelly | A61M 15/0028 128/203.12 |
| 2002/0065399 A1 * | 5/2002 | Stevenson | A61K 9/0075 530/399 |
| 2005/0066961 A1 | 3/2005 | Rand | |
| 2005/0196345 A1 | 9/2005 | Diederichs | |
| 2007/0044793 A1 | 3/2007 | Kleinstreuer | |
| 2007/0175476 A1 | 8/2007 | Lipowicz | |
| 2011/0126830 A1 | 6/2011 | Djupesland | |

FOREIGN PATENT DOCUMENTS

| | | |
|---|---|---|
| WO | PCT/GB91/01147 | 1/1992 |
| WO | PCT/CH92/00164 | 3/1993 |
| WO | PCT/CH96/00430 | 6/1997 |
| WO | PCT/US97/00771 | 7/1997 |
| WO | PCT/GB97/03478 | 6/1998 |
| WO | PCT/CA98/00746 | 2/1999 |
| WO | WO99/46055 A1 | 9/1999 |
| WO | WO2002030501 A1 | 10/2001 |
| WO | 023051 | 4/2002 |
| WO | WO03/095011 A1 | 11/2003 |

* cited by examiner

INHALATION DEVICE AND METHOD FOR INHALING POWDERS

FIELD OF THE INVENTION

The present invention relates to method of dispersing powders and, in particular or in a preferred embodiment, to a method of inhaling powders and to a device for dispersing and, in particular or in a preferred embodiment, for inhaling powders.

BACKGROUND OF THE INVENTION

Dispersion of powders is important for a number of fields and, in particular, in the field of medicine. Inhalation has become the primary route of administration in the treatment of asthma and COPD and has been demonstrated and even commercialized for the treatment of systemic diseases such as diabetes. This is because, in addition to providing direct access to the lungs, medication delivered through the respiratory tract provides rapid and predictable onset of action and requires lower dosages compared to, for instance, the oral route where the active ingredient must first pass through at least part of the digestive tract before absorption into the bloodstream.

Pressurized metered dose inhalers (pMDIs) are a commonly used inhalation devices. Such devices comprise a canister containing a suspension of fine drug particles in a propellant. Upon actuation, the aerosol contents are expelled through a metering valve and a metered dose is propelled into the lungs of the patient. The biggest threat to the continued use of pMDIs is that they rely on certain propellants, namely chlorofluorocarbons (CFCs), which have been argued to contribute to the depletion of the ozone layer. pMDIs also require coordinated actuation and inhalation by the patient for proper lung deliver.

Alternately, numerous types of dry powder inhalers (DPIs) have been developed, in which the inhalation air of the patient is used for dispersing the drug particles. DPIs are user friendly, as they do not generally require coordination between actuation and inspiration. The powdered medicament can be arranged as unit dose containers, e.g. blister packs, cartridges or peelable strips, which are opened in an opening station of the device. Alternatively, the unit dose is measured from a powder reservoir by means of a metering member, e.g. a dosing cup.

For pMDIs and DPIs, deep lung deposition to targeted sites depends strongly on delivering particle doses in the correct size range. Excessively large particles tend to impact on surfaces in the upper airways due to their high inertia and excessively small particles tend to reach the same surfaces due to Brownian diffusion.

In DPIs, to increase flowability and dosing accuracy of the powdered medicament (the inhalation powder), fine "active" ingredient (e.g. drug) particles of respirable size are typically mixed with coarser carrier particles to form an ordered mixture, wherein the fine active particles are attached to the larger carrier particles. This technique complicates the powder aerosolization process and, in particular, necessitates the break-up of the active/carrier agglomerates before they enter the patient's mouth and throat, where individual large particles and agglomerated large and small active particles tend to deposit. Effective aerosolization and deagglomeration of the powder requires that forces exerted on particles (be they on exposed surfaces of the device, between active and carrier particles or between active and active particles) must be overcome under all expected inhalation profiles.

The aim of an inhaler devices is to produce a high Fine Particle Dose (FPD) of particles in the respirable size range. However, the ability of a device to aerosolize and deagglomerate the active particles into a respirable particle size range depends on the patient's inspiration technique for most DPIs currently available. An ideal dry powder inhaler would provide uniform powder aerosolization and deagglomeration over a wide range of inhalation profiles, so as to generate consistent doses of respirable particles in the final dispersion.

Various techniques have been used in DPIs to aerosolize and deagglomerate active powder during inhalation. These include turbines and impellers (e.g. U.S. Pat. Nos. 4,524,769, 3,831,606 and 5,327,883) or other mechanical means (WO 98/26828), compressed gas (e.g. U.S. Pat. Nos. 5,113,855, 5,349,947 and 5,875,776), cyclones (e.g. U.S. Pat. No. 5,301,666 and WO 99/07426), electrostatic suspension and piezoelectric vibration (e.g. U.S. Pat. No. 3,948,264 and WO 97/26934), venturis (U.S. Pat. Nos. 4,200,099, 4,240,418 and WO 92/00771) and impactors (U.S. Pat. No. 5,724,959). Several patents have used electronic or other means of sensing of the airflow or pressure drop through the device to trigger the release of the powder into the airstream so as to coordinate activation of release and inhalation (e.g. WO 93/03782, WO 97/20589 and U.S. Pat. No. 5,388,572) or a means to mechanically control the patient's inspiration rate (U.S. Pat. Nos. 5,727,546 and 5,161,524). In general, these DP's have become more complicated and expensive.

Current passive devices operate in a range where a change in the flow rate or pressure drop across the device (which translates into a change in the turbulence experienced by the aerosol particles) leads to very significant changes in the aerosol particle distribution in the patient's lungs. Existing methods for inhaling dry powders for the delivery of active pharmaceutical agents (API) are limited by the low flowability and dispersability of inhalation powders. Recent developments in powder formulation technologies have produced highly flowable and dispersable powders of ideal size for delivery to the deep lung as has been shown in, for instance, WO 2007/125159.

The current invention offers a means to overcome the limitations of the existing inhalation methods and devices by offering a simple, low cost, high efficiency, safe and user friendly inhalation technology which is a benefit to industry and commerce.

PURPOSE OF THE INVENTION

The purpose of the present invention is to provide a means of overcoming the difficulties of existing powder aerosolization and dispersion techniques to provide a small and convenient delivery device for safe and effective dispersion and delivery of fine powders of, for instance, API's. The method can be used to create an aerosol cloud from a powder, direct an aerosol cloud or, in particular or in a preferred embodiment, to deliver a powder to the deep lung and to provide a device capable of carrying out said means. The technology may also be applied for powder delivery to other destinations such as the nasal membrane, to expel a cloud of powder into a vessel or open space or to direct a cloud or powder, for instance, a powder containing an irritant, to, for instance, the face and/or eyes of an attacker.

SUMMARY OF THE INVENTION

An aspect of embodiments of the present invention is focused on a method for delivering an aerosol of powder, preferably inhalation powder, having the following steps:

a) Providing powder positioned in a passage wherein the passage has one or more exits, one or more inlets and one or more obstructions to block the movement or to contain the powder within the passage before use;
b) Applying a breaching pressure differential between the one or more exits and the one or more inlets of the passage to breach the one or more obstructions so as to generate a flow through the passage;
c) Fully or partially aerosolizing the powder by means of the generated flow;
d) Releasing all or part of the fully or partially aerosolized powder from the passage.

Another aspect of embodiments of the present invention is focused on a device for dispersing and/or delivering a powder or an aerosol of powder, preferably an inhalation powder, having all or part of said powder positioned in a passage wherein the passage has one or more exits, one or more inlets and one or more obstructions to block the movement or to contain the powder within the inhalation device before use, the one or more obstructions being breachable up the application of a pressure differential between the one or more exits and inlets of the passage.

A device or inhalation device is understood to be any device suited to carrying out the described method for dispersing and/or delivering powder or an aerosol of powder.

A device is said to be activated or in use when a breaching pressure differential has been applied.

Inhalation is also understood to cover "negative" inhalation (i.e. exhalation or blowing), sucking or any other means to generate a pressure differential across the passage and/or obstruction. More generally, inhalation (and exhalation) are understood to mean applying an overpressure to an inlet and/or applying an underpressure to an outlet of the inhalation device.

A powder is to be understood to mean a collection of small particles or granules having, at least, a solid surface and wherein individual particles have a mean diameter preferably below one millimeter. A powder may contain particles of varying size and varying size distributions. For instance, an inhalation powder may contain large particles which may tend to be more flowable as powder and small particles which may tend to be more suitable to be delivered to the deep lung.

An inhalation powder is to be understood here broadly to cover all powders having at least a fraction of inhalation particles of appropriate size to be inhaled, sucked or blown into the mouth, throat or lung, or any other external or internal surface, passage, cavity or protuberance of an organism. Examples of inhalation powders include, but are not limited to, pharmaceutical, medicinal, diagnostic, irritant, poisonous, placebo, flavoring or scent giving agent or a powder intended to have biological, chemical, medicinal or psychological effect on an organism or other powders intended to have an effect, for instance, biological, chemical, medicinal, psychological or other on an organism. For clarity, inhalation powders also include exhalation powders.

Active ingredient and Active Pharmaceutical Ingredient (API) are here understood to mean any ingredient meant to produce an effect, positive or negative, on an organism. This may include, but are limited to, medicinal agents and drugs, diagnostic agents, irritants and poisons.

A passage here means a duct, passage, channel, tube or conduit and is to be understood to here broadly mean a structure having one or more inlet orifices (inlets) and one or more outlet orifices (outlets) through which a fluid (such as a liquid, gas, aquasol or aerosol) can pass. For clarity, this includes a structure which will allow a fluid to pass once an obstruction inhibiting its flow is breached. Thus, a blocked passage which does not allow the flow of a fluid from an inlet to an exit, but which would allow the flow when an obstruction is breached, also constitutes a passage. Thus, a passage is so defined as to include a blocked passage which may become unblocked upon activation or breaching. Examples include but are not limited to tubes, vessels with multiple orifices, straws and pipes, but more complex shapes are also possible according to the invention.

Breaching or activation is understood to mean dislocating, opening, rupturing or otherwise fully or partially removing or impairing or inhibiting an obstructions primary function (i.e. blocking a flow through a passage). For clarity, the terms breach, breached, activate or activated shall be used for any of these circumstances or their functional equivalents, e.g., a passage or device is activated when an obstruction is breached.

The one or more inlets and outlets according to the invention can be dependent on the direction of the pressure differential under inhalation, the higher pressure orifice(s) being the inlet(s) and the lower pressure orifice(s) being the outlet(s). In use, which orifice or orifices are inlets and/or outlets can depend on over which orifices and/or in which direction the breaching pressure differential is applied.

An obstruction is to be understood here to mean any structure or combination of structures that block the free flow of fluid, powder and/or aerosol out of the device. These can be either upstream or downstream of the powder or both upstream and downstream of the powder. Thus, an obstruction can, for instance block the airflow and aerosol powder flow (e.g. a diaphragm or membrane having low or no porousity), or can allow the airflow, but block the powder flow (e.g. a particle filter). For clarity, upstream and downstream refer to the conditions within the passage once an obstruction that blocks the fluid flow has been breached. Examples of obstructions include but are not limited to, for instance, valves, shutters, apertures, diaphragms, meshes, fabrics, films, filters, foils, membranes, covers, hatches, caps, doors or any other such device or construction which can fully or partially open under a pressure differential. The device according to the invention has at least one, but in many examples at least two obstructions which are between the inlet and the powder and between the outlet and the powder, but other configurations are possible according to the invention. It is preferable, though not necessary, that the obstruction also serves to aid in protecting the powder from external environment conditions such as moistures, oxidants, reducing agents, contaminants, electromagnetic radiation (e.g. UV light), heat, bacteria and other agents or conditions that may degrade or otherwise alter the powder before use.

Sufficient or breaching pressure differential is here understood to mean a pressure differential between the one or more inlets and one or more outlets of the one or more passages above the normal range of pressure differentials that typically exist in the use environment of the device before activation but below the maximum pressure differential a pressure differential generating agent (such as a pump or organism) produces (e.g. with its respiratory system) before or during use. For a given embodiment, said pressure differential is termed the release, breaching or initiation pressure differential.

A pressure differential generating agent is here understood to mean any agent that is able to generate a breaching pressure differential across at least one of the one or more obstructions in the inhalation device.

An organism is here understood to mean any organism able to generate a breaching pressure differential, e.g. through inhalation. Examples include but are not limited to reptiles, birds, and mammals (including humans).

DETAILED DESCRIPTION OF EMBODIMENTS OF THE INVENTION

An explanation of principles of the present invention follows based on the examples described below.

Figure 1A:
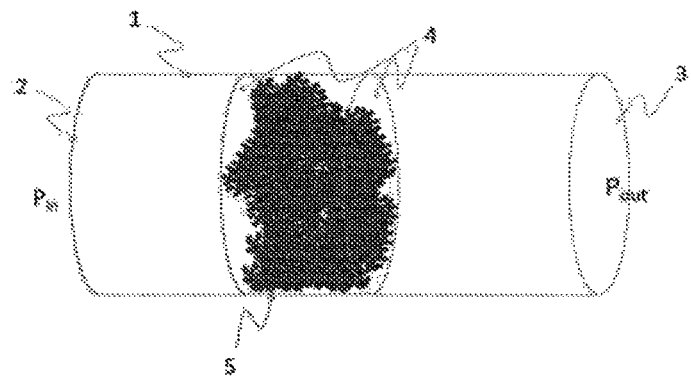
FIG. 1 illustrates a preferred embodiment of the invention in asymmetric (a) and symmetric (b) versions before activation when the pressure differential between the inlet and outlet of the device has not yet reached the breaching pressure differential.
Figure 1B:
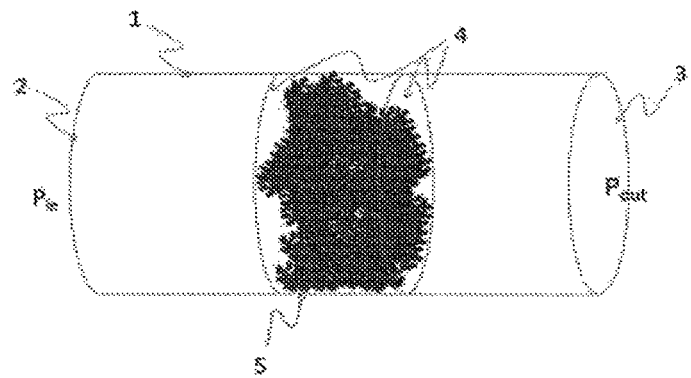

FIG. 1 shows a preferred embodiment of the invention before activation (i.e. before the breaching pressure differential is reached) where the passage (1) is a straight tube having an inlet (2) at pressure Pin and an outlet (3) at pressure Pout. Before use, Pout and Pin are essentially the same. In the preferred embodiment, the inner diameter of the tube is between 100 mm and 0.1 mm and more preferably between 10 mm and 1 mm and more preferably between 5 mm and 2 mm and most preferably, approximately 3.5 mm.

More complex ducts/passages/conduits are possible according to the invention. For more complex geometries, the diameter can be translated in terms of an equivalent cross sectional area or hydraulic diameter. The pressure differential (dP) is the absolute value of the difference between in inlet and outlet pressure. Before activation or in storage, the pressure differential is maintained below the breaching pressure differential (dPB). In the embodiment of FIG. 1, the two obstructions (4) are metal foil diaphragms sealed at the inner wall of the duct. Other materials and configurations are possible according to the invention such as polymers, organic membranes and papers or combinations thereof so long as they are only breached when the breaching pressure differential is reached. Preferable materials for the obstruction are also barriers against, for instance, water, oxygen, UV light, viruses, bacteria or other environmental factors that can degrade or otherwise affect the inhalation powder or the efficacy of the inhalation powder. One or both may also be sealed at one or both ends of the ducts, though, in the preferred embodiment, they are positioned at a sufficient distance from the end so as not to be susceptible to accidental puncture or rupture during normal handling before use. The powder (5) is located in the passage between the obstructions.

Figure 2:
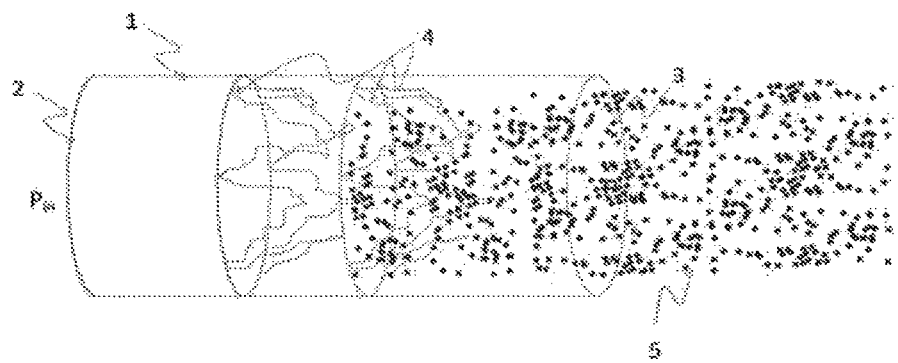
FIG. 2 illustrates a preferred embodiment of the invention during use when the pressure differential between the inlet and outlet of the device has reached the breaching pressure differential and a flow has been established to aerosolize the powder and carry it from the device.

FIG. 2 shows the preferred embodiment of FIG. 1 of the invention after activation (i.e. immediately after the breaching differential pressure has been reached) and wherein the passage (1) (also referred to as a duct or conduit) is a straight tube having an inlet (2) at pressure Pin and an outlet (3) at pressure Pout. In this embodiment of the invention, the two foil diaphragm obstructions rupture due to the pressure differential and the powder (5) is released from the volume between the obstructions (4) and flows to exit the tube through the exit orifice (3). Here dPB is preferably between 0.01 and 100 kPa, and more preferably between 0.1 and 10 kPa and more preferably between 0.5 and 5 Pa and most preferably between 1 and 3 kPa when the obstruction is breached.

According to certain embodiments an inhalation device comprises at least one inhalation powder positioned in at least one passage. The at least one passage has at least one exit, at least one inlet and at least one obstruction there between. One or more of the obstructions is capable of blocking the movement of or containing the inhalation powder within the inhalation device before use. The at least one obstruction of a passage becomes breachable upon the application of a pressure differential between the at least one exit and inlet of the passage. According to certain embodiments, the pressure differential required for the obstruction to become breachable must also be sufficient to at least partially aerosolize the inhalation powder.

In the preferred embodiment, when used for pulmonary deliver of powder, the average aerosolized inhalation particle agglomerate is preferably less than 1000 microns in diameter and more preferably less than 100 microns in diameter and more preferably less than 10 microns in diameter and most preferably approximately 3 microns in diameter. In the preferred embodiment the average aerosolized inhalation particle is preferably between 0.01 and 1000 microns in diameter and more preferably between 100 and 0.1 microns in diameter and more preferably between 10 and 1 microns in diameter and most preferably approximately 3 microns in diameter. In the preferred embodiment of the invention, inhalation particle agglomerates contain, on average, less than 1000 inhalation particles and more preferably less than 100 inhalation particles and more preferably less than 10 inhalation particles and more preferably less than 5 inhalation particles and more preferably less than 3 inhalation particles and most preferably 2 or less inhalation particles.

In the preferred embodiment of the invention, the fine particle fraction (FPF) of aerosolized inhalation powder particles is above 10% and more preferably above 50% and more preferably above 75% and more preferably above 85% and more preferably above 90% and more preferably above 95% and more preferably above 98% and most preferably above 99%. FPF is defined as fraction of particles emitted from the device that are below 5 micron in aerodynamic diameter.

In the preferred embodiment of the invention, when used for pulmonary delivery, the difference in emitted dose (ED) between a low inhalation rate and a high inhalation rate is below 80% and more preferably below 50% and more preferably below 30% and more preferably below 15% and more preferably below 10% and more preferably below 5% and more preferably below 2% and most preferably below 1% where the low inhalation rate is preferably below 117 LPM and more preferably between 1 and 53 LPM, and more preferably between 12 and 37 LPM and more preferably between 17 and 29 LPM and more preferably between 20 and 25 LPM and more preferably between 21 and 23 LPM and most preferably approximately 22 LPM and where the high inhalation rate is preferably above 1 LPM and more preferably between 24 and 117 LPM, and more preferably between 40 and 85 LPM and more preferably between 48 and 69 LPM and more preferably between 52 and 61 LPM and more preferably between 54 and 57 LPM and most preferably approximately 55 LPM.

Figure 3:
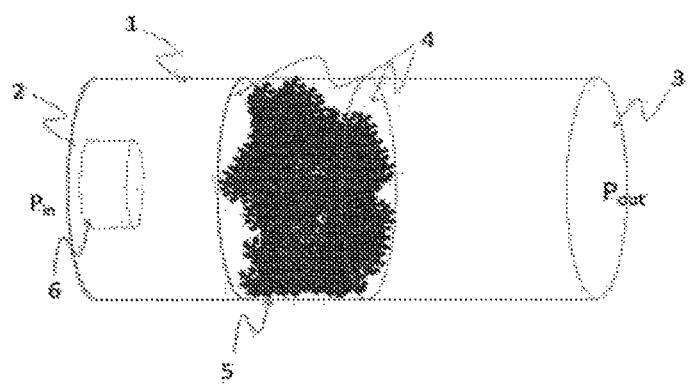
FIG. 3 illustrates a preferred embodiment of the invention before activation having an inlet or upstream constriction.

According to the invention, the cross sectional area of the passage can vary with the range of acceptable equivalent inner or hydraulic diameters. For instance, in another embodiment of the present invention is shown in FIG. 3 which also includes an upstream constriction (6), in this case in the form a step, to increase the pressure drop across the passage. It can also serve to increase the turbulence, shear force and mixing to increase the emitted dose and fine particle fraction and, in the case of pulmonary delivery of inhalation particles, further improve deep lung deposition of the inhalation particles. Other upstream constriction, shear force or turbulence generating geometries are possible according to the invention.

Figure 4:
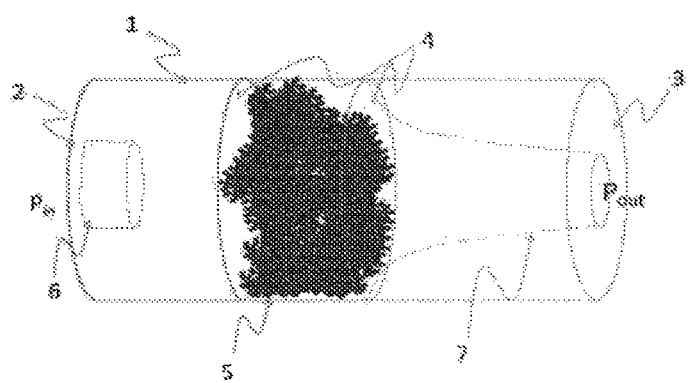
FIG. 4 illustrates a preferred embodiment of the invention before activation having an outlet or downstream constriction.

Another embodiment of the present invention is shown in FIG. 4 which also includes a downstream constriction (7), here in the form of a smooth converging nozzle, to control/increase the pressure drop across the passage and/or serve to increase the turbulence, shear force and mixing to increase the emitted dose and fine particle fraction and, in the case of pulmonary delivery of inhalation particles, further improve deep lung deposition of the inhalation particles. Other downstream constriction, shear force or turbulence generating geometries are possible according to the invention.

Figure 5:
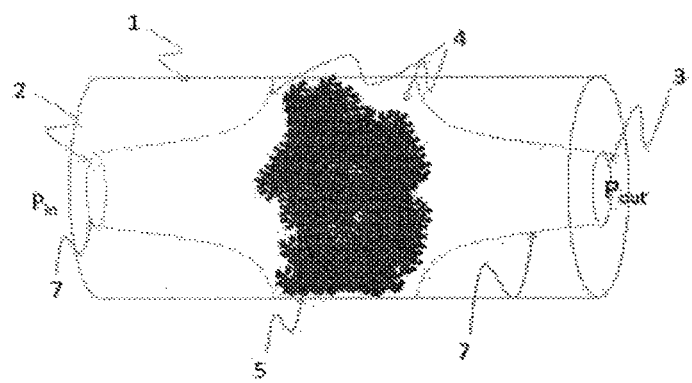
FIG. 5 illustrates a preferred embodiment of the invention before activation having both an outlet and an inlet constriction. Such a configuration is useful for storing the powder and/or protecting the powder from the environment.

Another embodiment of the present invention is shown in FIG. 5 which also includes multiple nozzle constrictions (7) to control/increase the pressure drop across passage and/or serve to increase the turbulence, shear force and mixing s as to increase the emitted dose and fine particle fraction and, in the case of pulmonary delivery of inhalation particles, further improve deep lung deposition of the inhalation particles.

Figure 6:
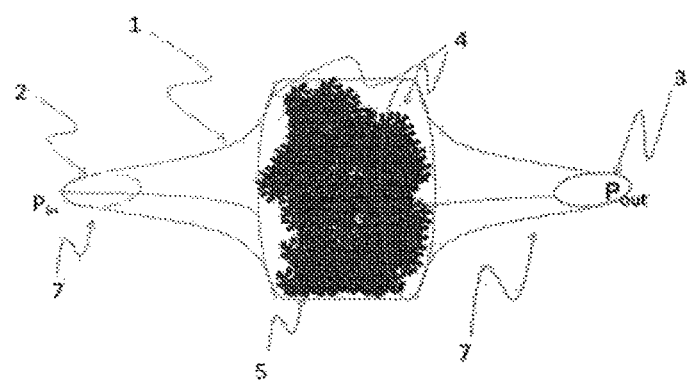
FIG. 6 illustrates a preferred embodiment of the invention before activation having both an outlet and an inlet constriction with both inlet and outlet shaped for easy sealing against the users' lips.

Another embodiment of the present invention is shown in FIG. 6 in which the inlet (2) and outlet (3) are made to be oval in shape in order to better and more comfortably seal against the lips of the user.

Figure 7A:
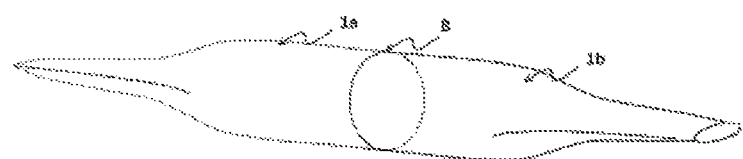
FIGS. 7a and 7b illustrate a preferred embodiment of the invention which allows the separate production and assembly of a sealed powder capsule in conjunction with a disposable or reusable passage.
Figure 7B:
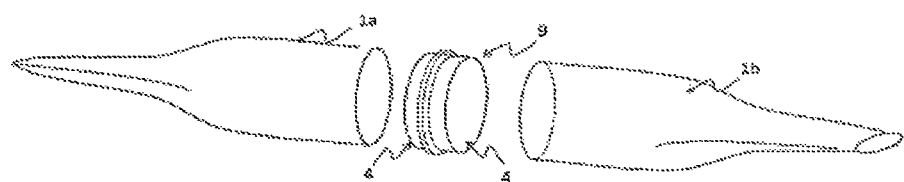

Another embodiment of the present invention is shown in FIGS. 7a and 7b which has a separable seam or break (8) in the passage (1) that allows a construction with three main elements. In this embodiment, the passage has two sections (1a and 1b) and the powder is contained within a sealed capsule (9) having a diaphragm or other appropriate breachable obstruction on both sides and containing one or more powders (5).

Figure 8A:
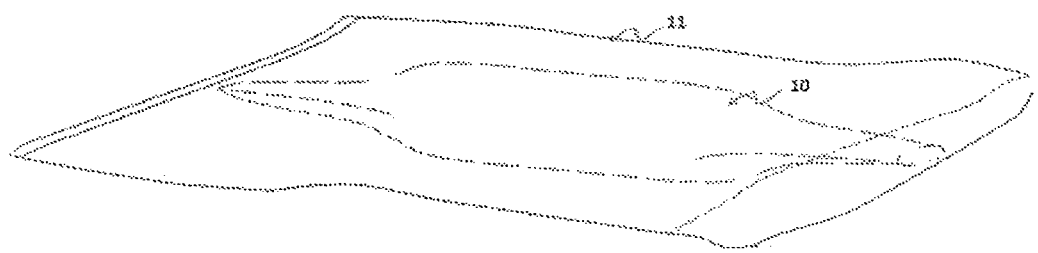
FIGS. 8a, 8b, 8c and 8d illustrate a preferred embodiment of the invention in which the entire device is stored in an individual sealed pouch for single use before disposal or refiling and in which the sealed powder capsule is stored in an individually sealed pouch before use before disposal or refiling.
Figure 8B:
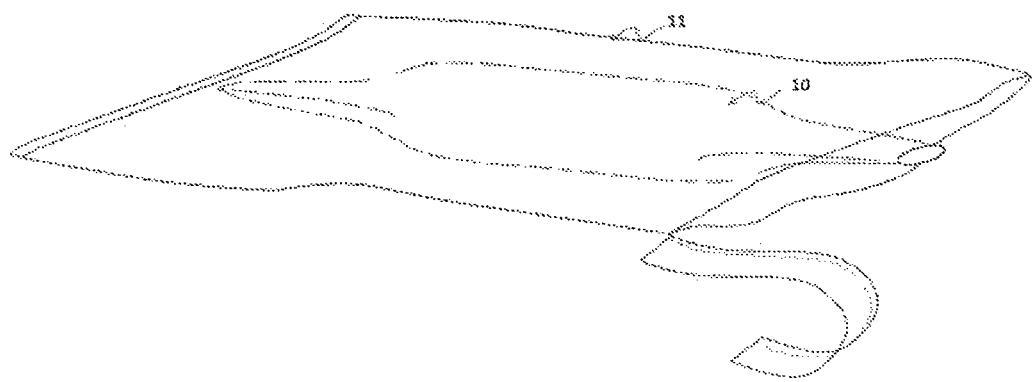
Figure 8C:
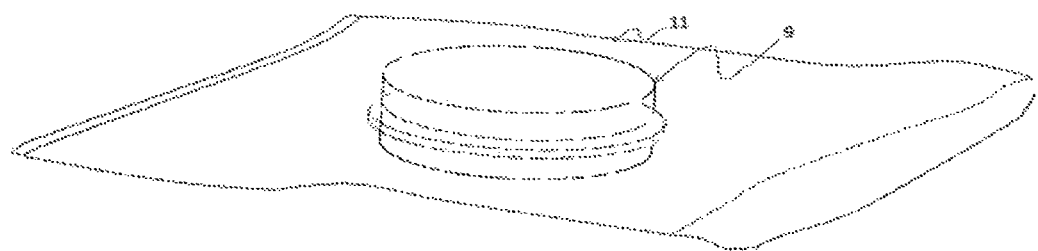
Figure 8D:
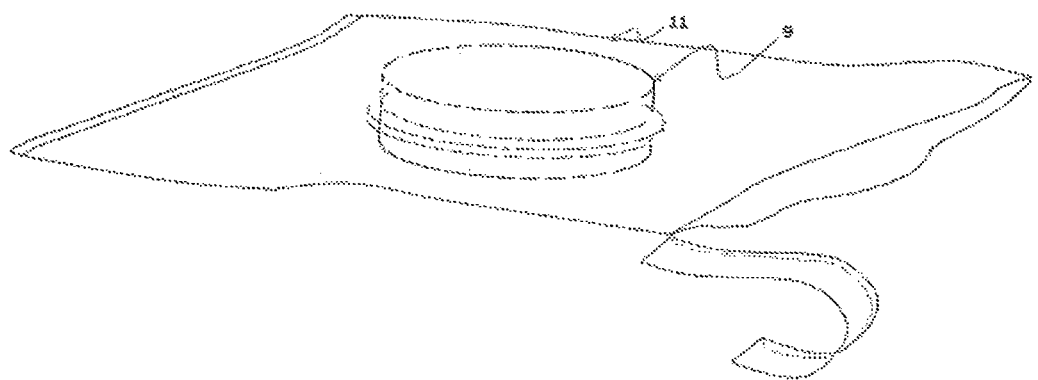

According to one embodiment of the present invention, as shown in FIG. 8, all or part of the entire device (10) is pre-assembled and packaged in a container for single dose use as shown in FIG. 8a, for instance, in a sealed package (11) which may be unsealed immediately prior to use as shown in FIG. 8b. The entire device (10) can then be disposed of or returned to a manufacturer or recycler for refilling. Conversely, the passage can be reused and a sealed capsule (9) can be inserted before each use. Thus, only the sealed capsule (9) is disposed of or returned to the manufacturer or recycler for reuse. In this case, as shown in FIGS. 8c and 8d, the sealed capsule (9) can be individually packaged for storage before use.

Figure 9A:
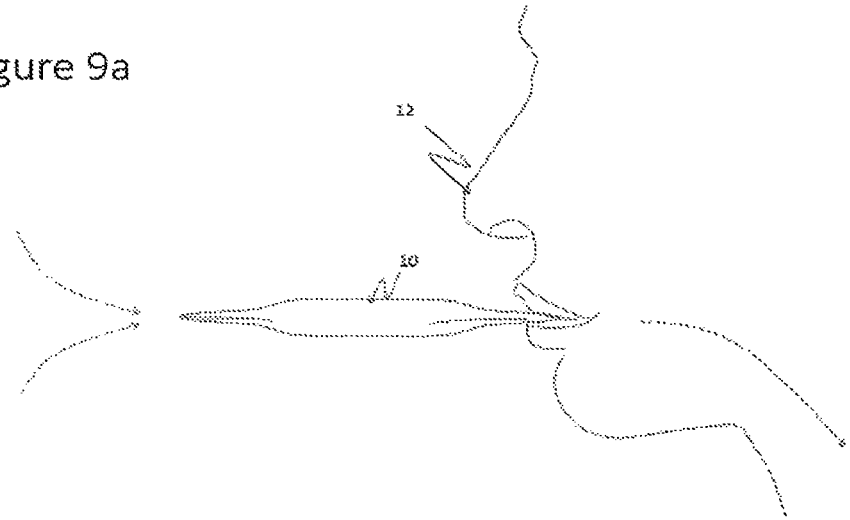
FIGS. 9a, 9b and 9c illustrate a preferred use of an embodiment of the invention in which a single user inhales through the device to draw the powder into the users mouth, throat and/or lungs (9a), a preferred use of an embodiment of the invention in which a first user exhales through the device to force the powder into a second users mouth, throat and/or lungs (9c) and a preferred use of an embodiment of the invention in a single user exhales through the device to deposit the powder onto a third users face or eyes (9b).
Figure 9B:
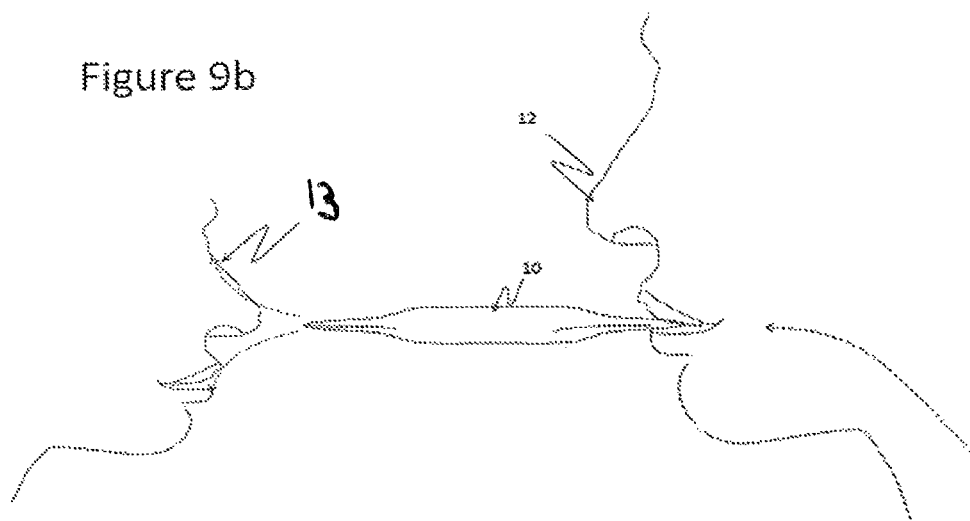
Figure 9C:
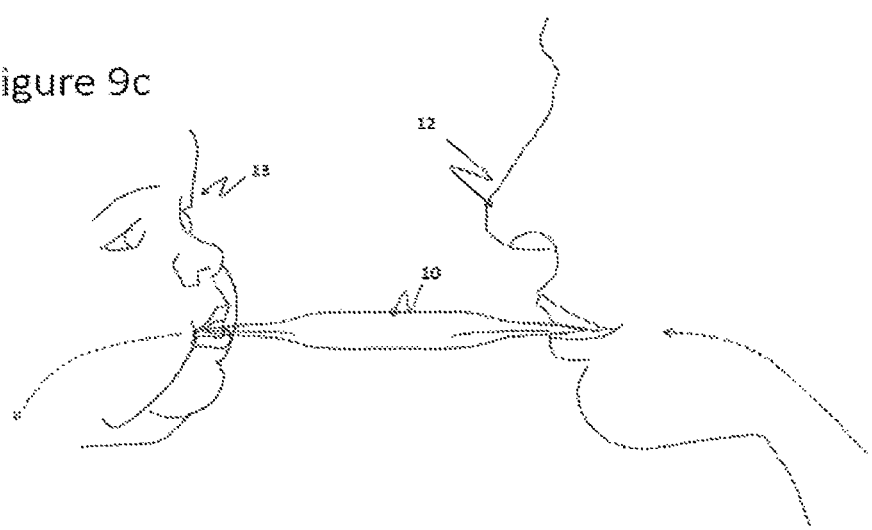

FIG. 9a shows a preferred use of an embodiment of the invention wherein a user (12) inhales through the device through the mouth so as to draw the powder into the user's mouth, throat and/or lungs. Similarly, an embodiment of the device can be configured for inhalation through the nose for delivery to the nasal cavity, throat or lungs. For delivery to the nasal cavity or throat, particles can be significantly smaller or larger than the optimal size for lung deliver. FIG. 9b shows a preferred use of the invention wherein a user (12) exhales through the device to deposit the powder into another user's (13) face or eyes. This use is appropriate for, for instance, applying an irritant an or a topical agent to a patient's or attacker eyes or skin. FIG. 9c shows a preferred use of the present invention, wherein the device is used by user (12) to deliver powder to another user (13). In this case, user (12) exhales (negatively inhales) or blows through the device (10) and the other user (13) either actively inhales or is passive and is exhaled into (i.e. is, at least partially, inflated). This use scenario is appropriate, for instance, for treating infants or very infirm patients who are not willing or not able to inhale powder on their own.

In any of these examples or other embodiments of the invention, a pump, bellows, vacuum, pressurized reservoir or other suitable pressure differential generating agent can be used in addition to or instead of inhalation (exhalation) by an organism.

It is important to note that, according to any of the configurations of FIGS. 1-9 or other embodiments of the invention, $P_{out}$ and $P_{in}$ can be reversed (i.e. the flow can go the opposite direction being shown and/or an exit in one use case can be an inlet in another use case), though certain configurations, such as FIG. 1b and FIGS. 5, 6, 7, 8 and 9, which are completely symmetric, operate essentially identically whichever direction the user inhales, exhales, sucks or blows and are, thus, less susceptible to misuse.

Figure 10:
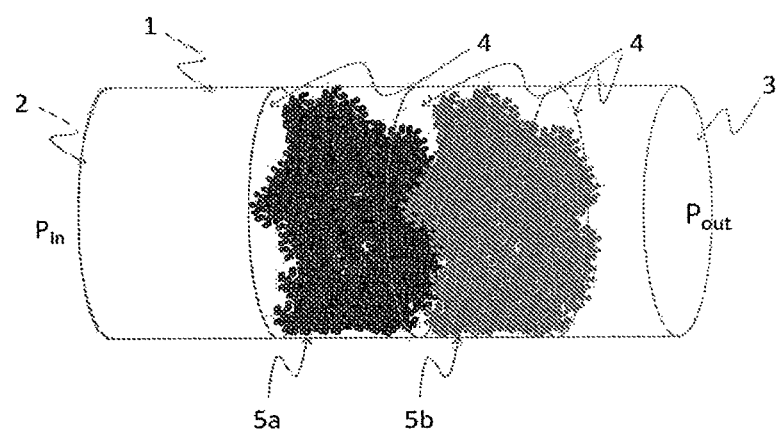
FIG. 10 illustrates an embodiment of the invention in which the inhalation device comprises two separate powders and two or more separate obstructions.

As shown in FIG. 10, in certain embodiments of the invention, the inhalation device comprises two or more separate passages and/or two or more separate powders (e.g. 5a and 5b) and/or two or more separate obstructions (4) in order to deliver one, two or more active agents and/or one, two or more doses either in parallel or in series.

As it is clear to a skilled person, the invention is not limited to the examples described above but the embodiments can freely vary within the scope of the claims.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A method for aerosolizing a powder comprising the steps of:
   a. providing a device having a passage with a powder between at least one exit and at least one inlet, and at least two flow blocking obstruction configured to block the movement or to contain the powder within the passage before use;
   b. generating a breaching pressure differential between the at least one exit and the at least one inlet of the passage by inhalation or exhalation to breach at least two flow blocking obstruction so as to generate a flow through the passage;
   c. at least partially aerosolizing the powder by the generated flow;
   d. releasing at least a portion of the aerosolized powder from the passage.
   e. wherein the two flow blocking obstructions are metal foil diaphragms sealed at an inner wall of a duct on both sides and containing one or more powders thereby forming a sealed membrane; and
   f. wherein the passage can be reused, and the sealed capsule can be inserted before each use such that only the sealed capsule is disposed or reused.

2. The method according to claim 1, wherein one or more of the flow blocking obstructions are valves, shutters, apertures, diaphragms, fabrics, films, foils, membranes, covers, hatches, caps, doors or a combination thereof.

3. The method according to claim 1, wherein the powder is an inhalation powder containing a pharmaceutical, a medicinal, a diagnostic, an irritant, a poisonous, placebo, a flavoring or a scent giving agent or a powder intended to have biological, chemical, medicinal or psychological effect on an organism.

4. The method according to claim 1, wherein the breaching pressure differential is above a normal range of pressure differentials that typically exist in the use environment before use but below a maximum pressure differential applied during activation and/or wherein the breaching pressure differential is between 0.01 and 100 kPa.

5. The method according to claim 1, wherein a passage cross sectional area and/or hydraulic diameter corresponds to an inner diameter of between 100 mm and 0.1 mm.

6. The method according to claim 1, wherein an average agglomerate of aerosolized powder particles is preferably less than 1000 microns in diameter and/or wherein the average aerosolized particle is between 0.01 and 1000 microns in diameter and/or wherein the average agglomerate of aerosolized powder particles is less than 1000 microns in diameter and/or aerosolized particle agglomerates contain, on average, less than 1000 inhalation particles.

7. The method according to claim 1, wherein a fine particle fraction (FPF) of aerosolized powder particles is above 10%.

8. The method according to claim 1, wherein a difference in emitted dose between a low inhalation rate and a high inhalation rate is below 80% where the low inhalation rate is below 117 LPM and where the high inhalation rate is above 1 LPM.

9. The method according to claim 1, wherein the device is single dose and/or disposable and/or wherein the device includes one or more separate passage components and one or more separate powder capsule components and wherein all or part of the passage component is reusable and/or wherein the one or more sealed capsules are single dose and/or disposable.

10. The method according to claim 1 wherein the pressure differential is generated by by, inhaling from, exhaling into, blowing from and/or sucking into one or more of the orifices in the inhalation device by one or more organisms and/or the inlet(s) and outlet(s) are determined according to the direction of the pressure differential applied.

11. An inhalation device comprising at least one inhalation powder positioned in at least one passage wherein the at least one passage has at least one exit, at least one inlet and at least two flow blocking obstruction positioned between the inlet and the exit, which is capable of blocking the movement of or containing the inhalation powder within the inhalation device before use and which is breachable upon the application of a pressure differential produced by inhalation or exhalation, sufficient to at least partially aerosolize the inhalation powder, between the at least one exit and inlet of the at least one passage of the inhalation device, wherein the two flow blocking obstructions are metal foil diaphragms sealed at an inner wall of a duct on both sides and containing one or more powders thereby forming a sealed membrane, and wherein the passage can be reused and the sealed capsule can be inserted before each use such that only the sealed capsule is disposed or reused.

12. The inhalation device according to claim 11, wherein one or more of the flow blocking obstructions are valves, shutters, apertures, diaphragms, fabrics, films, foils, membranes, covers, hatches, caps, doors, or combinations thereof.

13. The inhalation device according to claim 11, wherein the inhalation powder contains a pharmaceutical, a medicinal, a diagnostic, an irritant, a poisonous, a placebo, a flavoring or a scent giving agent or a powder intended to have biological, chemical, medicinal or psychological effect on an organism agent.

14. The inhalation device according to claim 11, wherein the breaching pressure differential is above a normal range of pressure differentials that typically exist in the use environment before use but below a maximum pressure differential applied during activation and/or wherein the breaching pressure differential is between 0.01 and 100 kPa.

15. The inhalation device according to claim 11, wherein a passage cross sectional area and/or hydraulic diameter corresponds to an inner diameter of between 100 mm and 0.1 mm.

16. The inhalation device according to claim 11, wherein an average agglomerate of aerosolized powder particles is less than 1000 microns in diameter and/or wherein the average aerosolized particle is between 0.01 and 1000 microns in diameter and/or wherein the average agglomerate of aerosolized powder particles is less than 1000 microns in diameter and/or aerosolized particle agglomerates contain, on average, less than 1000 inhalation particles.

17. The inhalation device according to claim 11, wherein a fine particle fraction (FPF) of aerosolized powder particles is above 10%.

18. The inhalation device according to claim 11, wherein a difference in emitted dose between a low inhalation rate and a high inhalation rate is below 80% where the low inhalation rate is below 117 LPM and where the high inhalation rate is above 1 LPM.

19. The inhalation device according to claim 11, wherein the device is single dose and/or disposable and/or wherein the device comprises one or more separate passage components and one or more separate powder capsule components and wherein all or part of the passage component is reusable and/or wherein the one or more sealed capsules are single dose and/or disposable.

20. A method for aerosolizing a powder, comprising:
a) providing a device having a passage with a powder between at least one outlet and at least one inlet, and at least two flow blocking obstructions configured to contain the powder within the passage before use, the at least one flow blocking obstruction being configured to breach at a predetermined pressure differential between the at least one outlet and the at least one inlet;
b) activating the device by inhalation or exhalation so as to at least partially aerosolize the powder and to release at least a portion of the aerosolized powder from the passage, wherein the device is activated upon an applied pressure differential reaching the predetermined pressure differential between the at least one outlet and the at least one inlet of the passage causing the at least two flow blocking obstructions to breach and generating a flow through the passage; and
c) wherein the two flow blocking obstructions are metal foil diapgragms sealed at an inner wall of a duct on both sides and containing one or more powders thereby forming a sealed membrane, and
d) wherein the passage can be reused, and the sealed capsule can be inserted before each use such that only the sealed capsule is disposed or reused.

* * * * *